United States Patent [19]

Karrasch et al.

[11] Patent Number: 4,573,980
[45] Date of Patent: Mar. 4, 1986

[54] PORT PROTECTOR

[75] Inventors: Frank Karrasch, Wadsworth; John F. Love, Palatine, both of Ill.

[73] Assignee: Baxter Travenol Laboratories, Inc., Deerfield, Ill.

[21] Appl. No.: 750,048

[22] Filed: Jun. 27, 1985

Related U.S. Application Data

[63] Continuation of Ser. No. 533,076, Sep. 19, 1983, abandoned.

[51] Int. Cl.⁴ ............................................. A61M 5/005
[52] U.S. Cl. .................................... 604/256; 604/408; 215/305; 215/320
[58] Field of Search .................... 604/29, 86, 256, 283, 604/408, 415, 905; 422/38; 138/96 R; 215/247, 255, 299, 305, 320, 317

[56] References Cited

U.S. PATENT DOCUMENTS

| | | |
|---|---|---|
| D. 273,227 | 3/1984 | Wilkinson . |
| 1,127,357 | 2/1915 | Gavaza . |
| 1,902,892 | 3/1933 | Pottenger, Jr. et al. . |
| 1,946,981 | 2/1934 | Lower . |
| 2,111,731 | 3/1938 | Reach . |
| 2,215,392 | 9/1940 | Freeman . |
| 2,372,182 | 3/1945 | Barr . |
| 2,704,100 | 3/1955 | Freeman . |
| 3,241,663 | 3/1966 | Kaepernik . |
| 3,307,552 | 3/1967 | Strawn ................................ 604/256 |
| 3,750,820 | 8/1973 | Labarre . |
| 4,046,276 | 9/1977 | Winchell et al. .................... 215/305 |
| 4,133,441 | 1/1979 | Mittleman et al. . |
| 4,160,473 | 7/1979 | Winchell ............................. 604/408 |
| 4,187,893 | 2/1980 | Bujan . |
| 4,244,480 | 1/1981 | Puig Planas ........................ 215/320 |
| 4,279,352 | 7/1981 | Ward . |
| 4,297,316 | 10/1981 | Cunningham . |
| 4,301,590 | 11/1981 | Ward . |
| 4,340,148 | 7/1982 | Beckham . |
| 4,362,158 | 12/1982 | Lena .................................... 604/415 |
| 4,379,472 | 4/1983 | Cunningham . |
| 4,410,026 | 10/1983 | Boggs et al. ........................ 604/408 |

FOREIGN PATENT DOCUMENTS 2221354 10/1974 France ................................ 215/296
0006046 1/1916 United Kingdom ................ 215/296

Primary Examiner—C. Fred Rosenbaum
Assistant Examiner—Michelle N. Lester
Attorney, Agent, or Firm—Paul C. Flattery; Garrettson Ellis; Daniel D. Ryan

[57] ABSTRACT

An elastic port protector closing the end of a tubular port, typically on a peritoneal dialysis solution or parenteral solution bag. The port protector defines an outer tubular section having inner and outer ends, and with an inner diameter which is less than the outer diameter of the tubular port on which it is intended to reside. An inner tubular section is connected to the outer tubular section at the outer end and is capable of occupying the bore of the outer tubular end in telescoping relation thereto. The inner tubular section has an outer diameter greater than the inner diameter of the tubular port, to fit into the bore of the tubular port in sealing relation. Handle means is carried on the outer tubular section to aid in removal of the port protector.

1 Claim, 6 Drawing Figures

FIG. 1
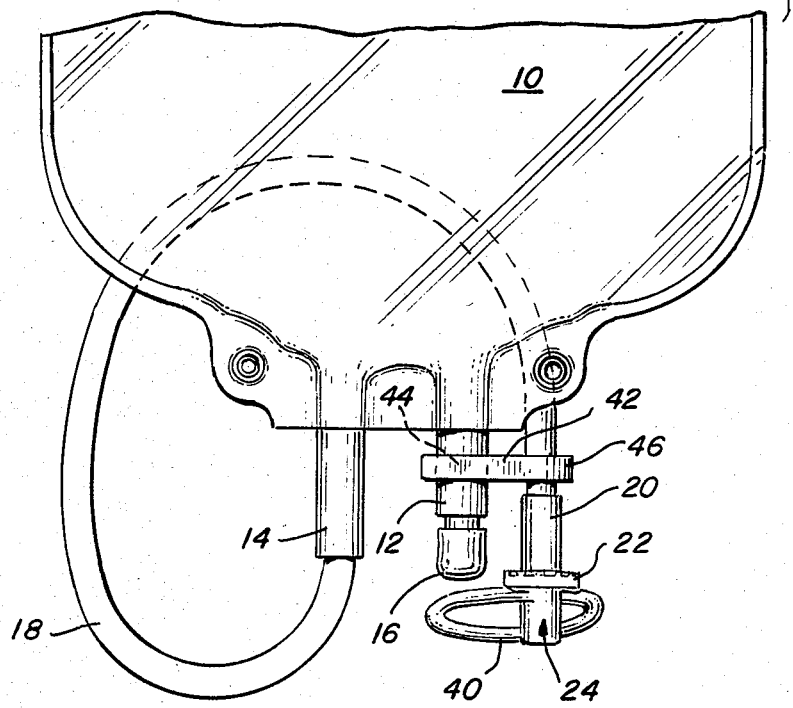
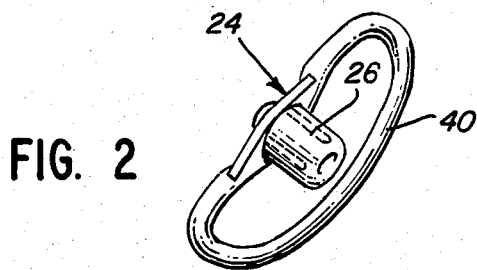
FIG. 2

PORT PROTECTOR this is a continuation of application Ser. No. 533,076, filed Sept. 19, 1983, now abandoned.

TECHNICAL FIELD AND PRIOR ART

This application relates to an improvement in elastic port protectors which are provided particularly for use in medical equipment to maintain access ports of medical containers of parenteral or peritoneal dialysis solution, for example, or access ports on various sets, in aseptic condition until used.

The VIAFLEX ® collapsible plastic container for parenteral solutions, and the DIANEAL ® peritoneal dialysis solution container, both sold by Travenol Laboratories, Inc. of Deerfield, Ill., each carry an injection site made of latex on the end of an injection port, surrounding the end of the access tube and defining inner and outer sleeves in telescoping relation, which respectively pass into the bore of the tube and surround the exterior end thereof. The inner latex sleeve of the port protector is open at its inner end, and connects to a needle pierceable wall at its outer end. The outer sleeve is also connected to the needle pierceable wall at its outer end. A similar structure, having a ring handle, is sold by Abbott Laboratories on peritoneal dialysis solution bags as a port protector.

The outer diameter of the inner sleeve cannot be easily made to exceed the inner diameter of the port in which it resides to improve the seal, since in that circumstance it could be installed into the bore of the port only with great difficulty. The outer sleeve folds around the port to provide a pressure seal.

In Cunningham U.S. Pat. No. 4,297,316 and its divisional U.S. Pat. No. 4,379,472, an end cap port protector is disclosed for thermoplastic tubing which is intended to receive a luer connector, to maintain the dimensional integrity during heat treatment for sterilization or the like. Here also, a latex structure is used having a projecting handle and inner and outer sleeves, the inner sleeve projecting into the bore of the thermoplastic tubing and the outer sleeve surrounding it. The outer end of the cap presents a closed surface to the exterior.

It would be desirable for improved sealing of the port end by the port protector for the inner sleeve to contribute more to the pressure seal formed about the tubular access port by pressure exerted between the outer and inner sleeves or tubular sections against the tubular port. This could be accomplished by causing the inner tubular sleeve to be of larger outer diameter than the inner diameter of the tubular port into which it penetrates. However, previous designs of port protectors would be exceedingly difficult to install into their position on the tubular port in this circumstance, so a compromise has, in the past, been required in which the inner sleeve of the port protector has an outer diameter that is not significantly larger than the inner diameter of the protected tubular port.

In accordance with this invention a port protector is provided, particularly for use with a solution container, which can provide a tighter seal because of a transversely enlarged inner sleeve or tubular section, which nevertheless can be easily installed into its desired position on the tubular port. Additionally, convenient handle means are provided for easy removal of the port protector with relatively low removing force. This is a particular advantage to some patients, for example patients on peritoneal dialysis who may be debilitated and exhibit significant physical weakness, so that they have great difficulty in performing normally simple tasks such as removing a port protector from the end of tubing.

DESCRIPTION OF THE INVENTION

In accordance with this invention an elastic port protector for closing the end of a tubular port is provided. The port protector comprises an outer tubular section defining, relative to an associated tubular port, inner and outer ends, and having an inner diameter which is typically less than the outer diameter of the tubular port in its normal, as-molded, unstressed condition.

An inner tubular section is connected to the outer tubular section at the outer end thereof, and is capable of occupying the bore of the outer tubular section in telescoping relation thereto. The inner tubular section typically has an outer diameter which is greater in its as-molded, unstressed condition than the inner diameter of the tubular port, to define a tubular space between the outer and inner tubular sections to receive the tubular port. The inner tubular section has a closed inner end and an open outer end.

Finally, handle means may be carried on the outer tubular section for ease of removal. The tubular port may be a solution container access port, with the end of the access port occupying the tubular space of the port protector. If desired, the port protector may be positioned on the end of a length of flexible tubing typically at least 20 cm. long, with the other end of the flexible tubing communicating with the solution container interior.

It is preferred for the handle means to connect to the outer tubular section at its inner end at a pair of exactly diametrically opposed positions. Under this circumstance, when one pulls the handle axially outwardly, the outer tubular section can easily fold outwardly for ease of peeling off the port protector, without having to frictionally slide it along the wall of the tubular port. This facilitates the removal of the port protector from the tubular port. Typically the handle means is of ring shape for easy grasping.

The elastic port protector of this invention may be fitted onto a tubular port with relative ease, using a probe member which passes into the bore of the inner tubular section and presses against the closed, inner end, to stretch the inner tubular section and drive it into the bore of the tubular port. As the inner tubular section is stretched, its diameter temporarily decreases, which further facilitates the installation. At the same time, the outer tubular section can be placed around the tubular port by a simple folding operation.

DESCRIPTION OF THE DRAWINGS

In the drawings, FIG. 1 is a fragmentary, plan view of a solution container incorporating the elastic port protector of this invention.

FIG. 2 is a perspective view of the port protector of FIG. 1.

DESCRIPTION OF SPECIFIC EMBODIMENTS

Figure 3:
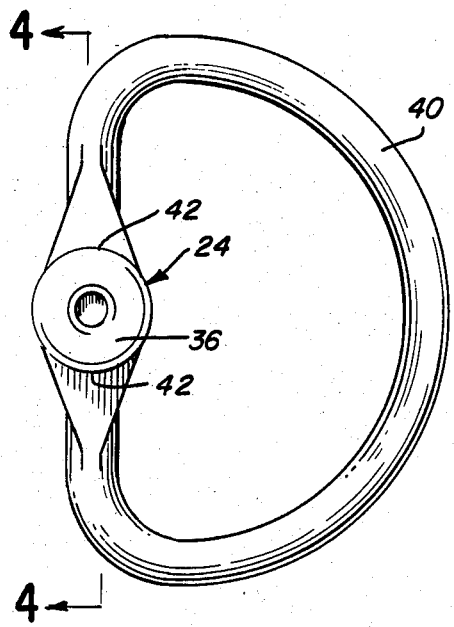
FIG. 3 is a plan view of the port protector of FIG. 2.

Referring to the drawings, FIG. 1 shows a generally conventional solution bag 10 made, for example, of polyvinyl chloride plastic, which may be used as a container for peritoneal dialysis solution. Bag 10 as shown defines a pair of ports 12 and 14, port 12 carrying a conventional latex injection site 16, for example of a type previously described. Port 14 carries a length of tubing 18, preferably in excess of 20 cm., at the end of which is a semirigid tubular connector 20 carrying flange 22 as shown. Port protector 24 fits over the end of tubular connector 20.

Port protector 24 comprises an outer tubular section 26 which defines, relative to associated tubular port 20, an inner end 28 and an outer end 30. Outer tubular section 26 defines an inner diameter in its unstressed condition which is less than the outer diameter of the tubular port 20. For example the unstressed inner diameter of section 26 may be about 0.24 inch, while the outer diameter of tubular port 20 may be 0.257 inch. It has been found that no mold draft is required for inner tubular section 32, but a small amount of draft (e.g., 1°) is desirably present for the outer tubular section 32 for ease of molding.

The inner diameter of tubular port 20 may in this circumstance be 0.193 inch, and the outer diameter of inner tubular section 32 may be about 0.20 inch.

Figure 4:
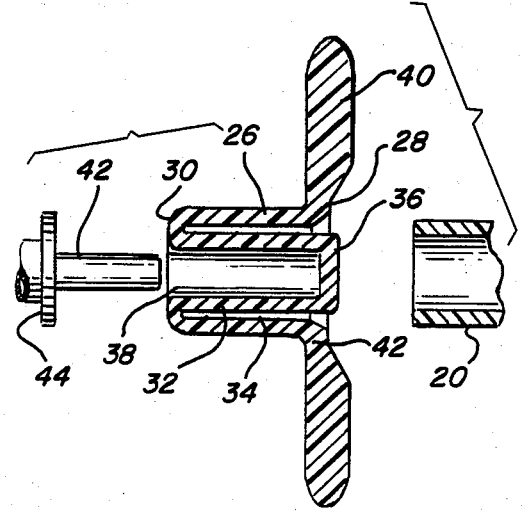
FIG. 4 is a longitudinal sectional view of the port protector of FIG. 2, prior to installation on a port.

Inner tubular section 32 may be connected to outer tubular section 26 at an annular convolution at end 30 as shown in FIG. 4. In other words, inner section 32 represents an integral extension of outer tubular section 26, which is folded or convoluted so as to occupy the bore of tubular section 26, defining a tubular space 34 therebetween.

Inner tubular section 32 defines a closed inner end wall 36 and an open outer end 38.

Handle means 40 is carried on outer tubular section 26, preferably being positioned at the inner end 28 of section 26. Handle means 40 may be a rod of material which is integral with the rest of port protector 24, being connected to outer tubular section 26 at a pair of exactly diametrically opposed positions 42. The effect of this is that when one pulls handle 40 axially, outer tubular section 26 convolutes or folds up in an annular convolution to easily peel off of tubular port 20 for removal, without having to frictionally drag port protector 24 across the surface of tubular port 20, which would greatly increase the pull-off force.

Figure 5:
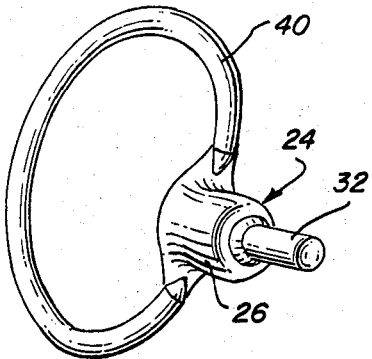
FIG. 5 is a perspective view of the port protector in its everted form, which it normally assumes upon removal from a port.

FIG. 5 shows port protector 24 in its everted form, following removal by pulling of ring handle 40. Thus, a debilitated person, as many patients who are on chronic peritoneal dialysis are, can be capable of removing the port protector of this invention. At the same time tubular port 20 can be under compressive pressure from both oversized inner tubular section 32 and undersized outer tubular section 26 for improved sealing.

Tubular port 20 may be made of a rigid or semirigid polyvinyl chloride formulation, while port protector 24 may be an integrally molded piece of elastomeric material, for example silicone rubber, or a thermoplastic organic elastomer such as Kraton G, sold by the Shell Chemical Company.

Figure 6:
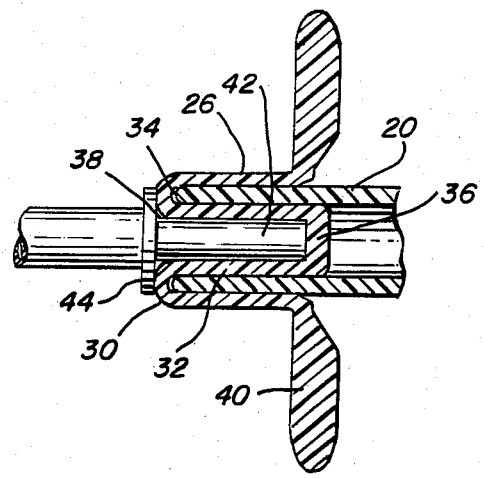
FIG. 6 shows the port protector of the previous drawings being installed on a port.

FIG. 6 shows how the port protector of this invention may be placed onto tubular port 20 with ease, despite the fact that the inner tubular section 32 may be of a larger outer diameter than the inner diameter of tubular port 20. Because end 38 of inner tubular section 32 is open, one may insert probe member 42 into the bore of inner tubular section 32 so that the end of probe member 42 presses inner end wall 36 into tubular port by a predetermined distance, until flange 44 of probe member 42 engages end 30 of port protector 24. Then probe member 42 may be withdrawn, and outer tubular section 26 may be folded around the exterior of tubular port 20 if necessary for complete installation.

As inner tubular section 32 is advanced by probe member 42, it is slightly stretched, causing it to temporarily reduce its diameter for easier sliding through tubular port 20. Upon removal of probe member 42, inner tubular section 32 retracts back toward its original, unstressed configuration, consequently increasing in diameter, to create the desired internal seal provided by the port protector of this invention.

Thus the port protector of this invention provides improved sealing over previous, related port protectors of the prior art, while at the same time the port protector is easily removed by pulling of the handle, particularly when it is a handle of the type shown, having diametrically opposed connections to outer tubular section 26. Other designs of handle may be used in this invention as may be desired.

As a further advantage of the port protector of this invention, the fact that the bore of inner tubular section 32 is open to the exterior helps to avoid differential pressure problems during sterilization cycles where there are significant pressure differentials. By this invention the sealed inside area volume around the bore is greatly reduced, which provides advantages in the sterilization process. Additionally, as described in the previously cited Cunningham patents, the tubular port can be protected during heat sterilization from deformation by the presence of inner tubular section 32. Increased protection is provided in this invention because of the greater compressive pressure provided by inner tubular section 32 against tubular port 20 during the heat sterilization processes.

Clip 42 may have an aperture 44 through which port 12 projects to carry clip 42. Tubing 18 can be carried in removable, frictional manner in a slot between jaws 46 for convenient retention of tubing 18 and port 20 until needed for use.

The above has been offered for illustrative purposes only, and is not intended to limit the scope of the invention of this application, which is as defined in the claims below.

That which is claimed is:

1. A port protector for closing the end of a tubular port, the port having an interior with an inner diameter and an exterior with an outer diameter, said port protector comprising means defining an elastic inner tubular member which, when unstretched, has a normal outer diameter which exceeds the inner diameter of the port, said inner tubular member being stretchable to reduce its normal outer diamter, said inner tubular member including an interior bore having a closed end and an axially opposite end which is open for accommodating within said interior bore the insertion of a push rod to press against said closed bore end to insert said inner tubular member into the interior of the port by stretching said inner tubular member to reduce said normal outer diameter, said elastic inner tubular member relaxing, upon removal of the push rod from said bore, to return toward said normal outer diameter, thereby sealingly occupying the interior of the port, means defining an elastic outer tubular member joined to said inner tubular member at a junction adjacent to said open end of said inner tubular member bore, said outer tubular member being normally folded back at said junction to peripherally surround said inner tubular member, said outer tubular member, when folded, having a normal, unstretched interior diameter greater than said normal outer diameter of said inner tubular member and less than the outer diameter of the port so that, when said inner tubular member sealingly occupies the interior of the port, said outer tubular member sealingly surrounds the exterior of the port, and means defining a handle joined to said outer tubular member at a point spaced away from said junction between said inner and outer tubular members, said handle being joined at said point at radially opposite portions of said outer tubular member, said handle being operative, in response to a pulling force applied along the axis of the port, for first peeling said elastic outer tubular member away from the exterior of the port until said junction between said inner and outer tubular members is reached and, in response to a continuation of said pulling force, for pulling said inner tubular member out of the interior of the port.

* * * * *